(12) United States Patent
Behrens et al.

(10) Patent No.: US 6,960,680 B2
(45) Date of Patent: Nov. 1, 2005

(54) MANUFACTURE OF WATER-SOLUBLE β-HYDROXYNITRILES

(75) Inventors: Carl Henry Behrens, Newark, DE (US); James Joseph Mencel, North Wales, PA (US)

(73) Assignee: Rhodia Chirex, Inc., Boston, MA (US)

( * ) Notice: Subject to any disclaimer, the term of this patent is extended or adjusted under 35 U.S.C. 154(b) by 0 days.

(21) Appl. No.: 10/338,814

(22) Filed: Jan. 8, 2003

(65) Prior Publication Data

US 2004/0133029 A1 Jul. 8, 2004

(51) Int. Cl.[7] .............................................. C07C 253/16
(52) U.S. Cl. ........................................................ 558/347
(58) Field of Search ........................................ 558/347

(56) References Cited

U.S. PATENT DOCUMENTS

5,136,079 A * 8/1992 Mitchell ...................... 558/347

FOREIGN PATENT DOCUMENTS

| DE | 3734219 A1 | 10/1987 | ......... C07D/303/36 |
| JP | 41-16504 | * 9/1966 | |
| JP | 1993310671 A | 11/1993 | ......... C07C/255/12 |
| WO | WO 00/46186 | 8/2000 | ......... C07C/255/20 |
| WO | WO 01/72698 A1 | 10/2001 | ......... C07C/255/11 |

OTHER PUBLICATIONS

Stanishauskaite, A. et al., "Some Transformations of N–(2–3,Epoxypropyl)–1,8–Naphthosultam," Chemiistry of Heterocyclic Compounds, 36(2), 195–200 (2000).

Catasus, M. et al., "A Totally Stereocontrolled Route to N–Methyl–γ–amino–β–hydroxy Acids: Asymmetric Synthesis of the Amino Acid Component of Hapalosin," Tetrahedron Letters 40: 9309–9312 (1999).

Castejón, P. et al., "Ready Access to Stereodefined β–Hydroxy–γ–amino Acids. Enantioselective Synthesis of Fully Protected Cyclohexylstatine," Tetrahedron Letters 52(20): 7063–7086 (1996).

Mitchell, D. and Koenig, T., "Regiospecific Opening of 1,2–Epoxides with Acetone Cyanohydrin under Mildly Basic Conditions," Tetrahedron Letters 33(23): 3281–3284 (1992).

Benedetti, F. et al., "Ring–Opening of Epoxyalcohols by Diethylaluminium Cyanide. Regio– and Stereoselective Synthesis of 1–Cyano–2,3–diols," Tetrahedron Letters 40: 1041–1044 (1999).

Klunder, J.M. et al., "Arenesulfonate Derivatives of Homochiral Glycidol: Versatile Chiral Building Blocks for Organic Synthesis," J. Am. Chem. Soc. 54: 1295–1304 (1989).

Li, Z. et al., "Hydrogen Bonding and Attenuation of the Rate of Enzymic Catalysis," J. Am. Chem. Soc. 120(50: 13003–13007 (1998).

Ooi, T. et al., "Facile and Selective Alkylation of 3,3,3–Trifluoropropene Oxide (TFPO) with Organoaluminum Reagents via Pentacoordinate Trialkylaluminum Complexes," Chemistry Letters 817–818 (1998).

Tsuruoka, A. et al., "Practical Oxirane Ring Opening With In situ Prepared LiCN; Synthesis of (2S,3R)–3–(2, 4–Difluorophenyl)–3–Hydroxy–2–Methyl–4–(1H–1,2, 4–Triazol–1–YL)–1–Butanenitrile," Synthetic Communications 27(20): 3547–3557 (1997).

Fuji, K. et al., "Ring Opening of Optically Active CIS–Disubstituted Aziridino Alcohols: An Enantiodivergent Synthesis of Functionalized Amino Alcohol Derivatives," Heterocycles 42(2): 701–722 (1996).

Kawabata, T. et al., An Enantiodivergent Synthesis of three ε–Amino Alcohols: Preparation of Key Intermediates for Bestain and the Related Peptides, Tetrahedron Letters 34(32): 5127–5130 (1993).

Ramachandran, P. et al., "Chiral Synthesis via Organoboranes, 40. Selective Reductions. 55. A Simple One–Pot Synthesis of the Enantiomers of (Trifluoromethyl)oxirane. A General Synthesis in High Optical Purities of a–Trifluoromethyl Secondary Alcohols via the Ring–Cleavage Reactions of the Epoxide," J. Org. Chem. 60: 41–46 (1995).

Takahashi, Kyoko et al., "A New Synthesis of HMG–CoA Reductase Inhibitor NK–104 Through Hydrosilylation–Cross Coupling Reaction," Tetrahedron Letters 34(51): 8263–8266 (1993).

Bessodes, M. et al., "A New, Versatile and Stereospecific Route to Unusual Amino Acids: The Enantiospecific Total Synthesis of Statine Amide and Its Three Stereoisomers," J. Org. Chem. 57: 4441–4444 (1992).

Ohno, H. et al., "Ring Opening of Epoxides with Acetone Cyanohydrine Catalyzed by Lanthanoid(III) Alkoxides," Chemistry Letters, pp. 975–978 (1993).

Effenberger, F. and Null, V., Enzyme–Catalyzed Reactions, 13(1),—A New, Efficient Synthesis of Fagomine, Liebigs Ann. Chem. pp. 1211–1212 (1992).

Ciaccio, J. et al., "Facile Conversion of Epoxides to β–Hydroxy Nitriles Under Anhydrous Conditions With LithiumCyanide," Tetrahedron Letters 33(11): 1431–1434 (1992).

Kasai, N. and Sakaguchi, K. "An Efficient Synthesis of (R)–Carnitine," Tetrahedron Letters 33(9): 1211–1212 (1992).

(Continued)

*Primary Examiner*—Johann Richter
*Assistant Examiner*—Ebenezer Sackey
(74) *Attorney, Agent, or Firm*—Ohlandt, Greeley, Ruggiero & Perle

(57) ABSTRACT

A process for making a water-soluble β-hydroxynitrile. A 1,2-epoxide and an inorganic cyanide salt are reacted in a solvent having aqueous methanol and a buffer therein to form β-hydroxynitrile. The buffer substantially inhibits the formation of reaction products other than β-hydroxynitrile. Optionally, water may be removed from the β-hydroxynitrile by azeotropic distillation with acetonitrile and subsequently purified via vacuum distillation and filtration.

22 Claims, No Drawings

OTHER PUBLICATIONS

Chini, M. et al., "Easy Direct Stereo– and Regioselective Formation of β–Hydroxy Nitriles by Reaction of 1,2–Epoxides with Potassium Cyanide in the Presence of Metal Salts," Tetrahedron Letters 32(36): 4775–4778 (1991).

Rosenberg, S. et al., "Novel Resin Inhibitors Containing Analogues of Statine Retro–Inverted at the C–Termini: Specificityat the P2 Histidine State 1,2," J. Med. Chem. 30: 1224–1228 (1987).

Behrens, C. et al., "Selective Transformation of 2,3–Epoxy Alcohols and Related Derivatives. Strategies for Nucleophilic Attack at Carbon–1," J. Org. Chem. 50: 5687–5696 (1985).

Rosenberg, Saul et al., Potent, Low Molecular Weight Renin Inhibitors Containing a C–Terminal Heterocycle: Hydrogen Bonding at the Active Site1.2, J. Med. Chem. 33 pp. 1582–1590 (1990).

Wade, P. et al., "Diastereofacial Selectivity Studies on 3–Alkenyl–4,5–Diphenyl–4,5–Dihydroisoxazoles," 55 pp. 3045–3051 (1990).

Fukuzawa, A. et al., "Synthesis of (6S,7S)–Trans–Laurediol and its [9,102H2]–Analogue," Tetrahedron Letters 27(25): 2901–2902 (1986).

Rico, I.and Lalo, J., "Inhibitors of Cholesterol Biosynthesis: New Route to Phosphonic Analogs of 3–Hydroxy–3–Methyl Glutaric Acid(Meglutol)," New Journal of Chemistry 13(7): 507–510 (1989).

Kim, J. et al., "Synthesis of 5–(5–Deoxy–β–D–Erythro–Pent–4–Enofuranosyl)–1,3–Dimethyluracil. A Potentially Versatile Intermediate1," J. Org. Chem. 53 pp. 5046–5050 (1988).

Voeffray, R. et al., "193. L–Carnitine. Novel Synthesis and Determination of the Optical Purity," Helvetica Chimica Acta. 70 pp. 2058–2064 (1987).

Cardani, S. and Pratt, L., Asymmetric Synthesis of Threo–(2S,3R)–2–Amino–3–hydroxypentanedioic Acid 5–Amide (threo–β–Hydroxy–L–glutamine)., Synthesis pp. 1032–1035 (1986).

Imi, K. et al., "Reaction of Cyanotrimethylsilane with Oxiranes. Effects of Catalysts or Mediators on Regioselectivity and Ambident Character," J. Org. Chem. 52 pp. 1013–1016 (1987).

Ko, S. et al., p–Nitrobenzoate Esters of Epoxy Alcohols: Convenient Synthons for Water–Soluble Epoxy Alcohols, J. Org. Chem 52 pp. 667–671 (1987).

Fujimoto, K. et al., "From Penicillin to Penem and Carbapenem. VII. Introduction of an Allyl Group at the C–4 Position of the Axetidimone Molecule, and the Synthesis of Dethiathienamycin," The Chem. Soc. of Japan 59(5): 1363–1369 (1986).

Fujimoto, K. et al., "From Penicillin to Penem and Carbapenem. Synthesis of Dethiathienamycin," Tetrahedron Letters 26(1): 89–92 (1985).

SciFinder Search Results—for databases Caplus, Chemcats And Chemlist no date available.

Vanhessche, Koen P.M. et al., "Catalytic Asymmetric Synthesis of New Halogenated Chiral Synthons," Chem. Eur. J., 3(4): 517–522 (1997).

Bessodes, M. Sarah M. and Antonakis, K., "An Enantiospecific and Versatile Synthesis of Statine," Tetrahedron Asymmetry, 2(2): 111–112 (1991).

Ruanox, Jose Luis Garcia et al., Basic Media Behavior of N–[2–(I–Hydroxy–2–Y–Ethyl)Phenyl] Ethyl Carbamates (Y×SMe, SOMe, SO2Me, II, Br, CN), Tetrahedron Letters 45(1): 203–214 (1989).

* cited by examiner

MANUFACTURE OF WATER-SOLUBLE β-HYDROXYNITRILES

BACKGROUND OF THE INVENTION

1. Field of the Invention

The present invention relates to processes for making water-soluble β-hydroxynitriles. The present invention more particularly relates to processes for making β-hydroxynitriles from terminal 1,2-epoxides and inorganic cyanides.

2. Description of the Prior Art

β-hydroxynitriles may be prepared via ring-opening reactions between epoxides and cyanides or cyanide equivalents. Methanol is commonly employed as a solvent in ring-opening reactions of terminal epoxides because some cyanides, particularly potassium cyanide, are moderately soluble therein. A problem, however, with the use of methanol is the possibility of side reactions forming undesirable by-products. Upon reaction of the terminal epoxide and potassium cyanide, a potassium alkoxide of a β-hydroxynitrile is formed. The potassium alkoxide is highly alkaline and, along with residual cyanides, renders the reaction product mixture very alkaline. The potassium alkoxide may then react with methanol to form potassium methoxide, which may then react with the epoxide to form a methyl ether, an undesirable by-product.

One means employed in the prior art to address the problem of undesirable side reactions when using methanol as a solvent is to lower the alkalinity of the product mixture by implementing acidic reaction conditions. This, however, is problematic because acidic conditions may result in runaway or accelerated ring-opening reaction rates as well as in industrial hygiene and safety issues.

Another problem encountered is isolating water-soluble β-hydroxynitriles from reaction product mixtures. Isolation of non-water-soluble β-hydroxynitriles has not presented problems since classical extraction and chromatographic techniques can be employed. However, such classical extraction techniques are not useful with water-soluble β-hydroxynitriles since they cannot be separated from residual cyanides or cyanide salts, which are also water-soluble.

Product color is another problem encountered during preparation of some water-soluble β-hydroxynitriles, particularly 3-hydroxyvaleronitrile. When β-hydroxynitriles are prepared via a ring-opening reaction from an epoxide and potassium cyanide, a dark-colored refined oil is obtained upon distillation. To be suitable for use, the dark distillate oil must be refined to further reduce impurities, which results in a lighter color or substantially colorless oil. Further refining of dark oil from conventional processes is difficult via conventional distillation techniques.

It would be desirable to have an improved process for preparing β-hydroxynitriles via ring-opening reactions between terminal 1,2-epoxides and inorganic cyanides. It would further be desirable to have a process whereby undesirable by-products are reduced or eliminated. It would further be desirable to have a process that enabled the separation of water-soluble β-hydroxynitriles from cyanide salts and residual cyanides. It would further yet be desirable to have a process for preparing β-hydroxynitriles wherein resulting distillate oils are lighter in color, e.g., a pale yellow color in the instance of 3-hydroxyvaleronitrile. It would further still be desirable to have a process for making β-hydroxynitriles that can easily be adapted to development or commercial scale.

SUMMARY OF THE INVENTION

According to the present invention, there is a process for making a water-soluble β-hydroxynitrile. The process comprises reacting a 1,2-epoxide and an inorganic cyanide salt in an aqueous organic solvent with a buffer to form β-hydroxynitrile. The buffer at least partially inhibits the formation of reaction products other than β-hydroxynitrile.

DETAILED DESCRIPTION OF THE PREFERRED EMBODIMENT

It was surprisingly found that a β-hydroxynitrile could be prepared via a ring-opening reaction between terminal 1,2-epoxides and inorganic cyanides while the incidence of undesirable by-products is reduced or eliminated. It was also surprisingly found that water-soluble β-hydroxynitriles could be isolated from cyanide salts and residual cyanides. It was also surprisingly found that reaction product mixtures having 3-hydroxyvaleronitrile could be directly obtained with a lighter color, i.e., a pale yellow, than reaction product mixtures obtained from conventional processes.

In one embodiment, the present process employs a buffer that substantially inhibits the formation of reaction products other than a β-hydroxynitrile. The buffer is capable of protonating the alkoxide generated during the epoxide ring opening reaction and substantially preventing a side reaction between the alkoxide and methanol. The buffer must be acidic enough to protonate the alkoxide yet not be so acidic as to excessively accelerate the ring-opening reaction or create other process control and/or hygiene problems. The buffer preferably has a $pK_a$ of between about 9.1 to about 13 and most preferably between about 10 to about 12. Suitable buffers include inorganic buffers, such as sodium bicarbonate or potassium bicarbonate, and organic buffers, such as phenol, succinimide, benzenesulfonamide, and combinations thereof. A preferred buffer is sodium bicarbonate.

Optionally, the present process may employ azeotropic distillation with acetonitrile to remove at least a portion of or substantially all the water from the product mixture having the β-hydroxynitrile. To effect the distillation, acetonitrile is added, i.e., blended with the product mixture in a certain proportion to form an azeotropic mixture with the water in the product mixture. The relative proportions of water and acetonitrile obtained during an azeotropic distillation will vary depending upon the composition of the product mixture, but will typically be between about 15 wt % to about 17 wt % for water and between about 83 wt % to about 85 wt % at atmospheric pressure for acetonitrile. The azeotropic temperature of boiling or distillation will typically range from between about 76° C. to about 82° C. at atmospheric pressure. Other useful azeotropes include toluene, acetone, and 2-butanone (methyl ethyl ketone).

Other conventional distillation processes may optionally be employed in the present process to assist in the recovery of the product and to remove solvents, impurities, and by-products. Distillation may be employed at atmospheric pressure, elevated pressure, or under reduced pressure or vacuum.

Further optionally, the present process may employ filtration to help purify the reaction mixture and/or product mixture. Filtration may be employed one or more times between or after distillation runs to remove various inorganic salts that precipitate from the reaction/product mixtures. The inorganic salts are predominantly chemically related to the buffer. In a preferred process, a slight deficiency of cyanide relative to epoxide is used, so there are typically little, if any, salts chemically related to the cyanide salts. Any conventional filtration medium can be used, such as filter paper, cloth, and silica gel with or without anhydrous sodium sulfate. The silica gel and anhydrous sodium sulfate serve a dual function as a filtration medium and a desiccant. Filtration may be vacuum or pressure assisted or may be unassisted. After filtration, the filtration medium may optionally be washed with a suitable solvent, such as methylene chloride, to ensure that substantially all of the product is collected.

The product takes the form of an oil. An advantage of the present process is the ability to obtain product oils of high purity that are light yellow or colorless depending upon the degree of purity desired. These are in contrast to the dark, heavy oils obtained when employing conventional processes.

In a preferred process, the reaction mixture is purified by employing one or more azeotropic distillations to remove water, one or more conventional distillations to remove methanol and 1, 2-epoxides, one or more filtrations between distillations to remove inorganic salts. The azeotropic distillation of the reaction mixture typically produces product oils of light yellow color. Conventional distillations may be used to render the oil colorless. Vacuum distillations, e.g. carried out at about 3 torr or less, especially high vacuum distillations, e.g. carried out at about 0.5 torr or less, are particularly useful in obtaining product of high purity. High vacuum distillations wherein the product itself is distilled, condensed, and collected are particularly useful.

The present process is useful in making a variety of water-soluble product β-hydroxynitriles. Suitable β-hydroxynitriles are those corresponding to the product in the following reaction sequence:

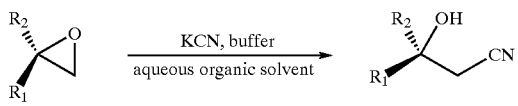

wherein $R^1$ and $R^2$ are, independently, hydrogen or methyl, ethyl, n-propyl, i-propyl, t-butyl, phenyl, $(CH_2)_nX$, $COR^3$, $CO_2R^3$, or $S(O)_mR^3$ groups; and wherein X is, independently, a phenyl, $COR^3$, $CO_2R^3$, $S(O)_mR^3$, $OR^3$, $NR^3R^4$ or $N(O)R^3R^4$ group; and wherein $R^3$ and $R^4$ are, independently, hydrogen or a methyl, or ethyl group; and wherein n is, independently, 1 or 2 and m is, independently, 0, 1, 2, or 3.

The product β-hydroxynitriles may be racemic or enantiomerically enriched or pure. Preferred product β-hydroxynitriles have structures wherein $R^1$ and $R^2$ are, independently, hydrogen or a methyl, ethyl, $(CH_2)_nX$, $COR^3$, $CO_2R^3$, or $S(O)_mR^3$ group; X is, independently, a $COR^3$, $CO_2R^3$, $S(O)_mR^3$, $OR^3$, $NR^3R^4$, or $N(O)R^3R^4$ group; $R^3$ and $R^4$ are, independently, hydrogen or a methyl group; n is 1; and m is, independently, 0, 1, 2, or 3. More preferred product β-hydroxynitriles have structures wherein $R^1$ and $R^2$ are, independently, hydrogen or a methyl, ethyl, $(CH_2)_nX$ group; X is, independently, a $COR^3$, $CO_2R^3$, $S(O)_mR^3$, $OR^3$, $NR^3R^4$ group; $R^3$ and $R^4$ are, independently, hydrogen or a methyl group; and n is 1; and m is, independently, 0, 1, 2, or 3. Most preferred product β-hydroxynitriles have structures wherein $R^1$ is ethyl and $R^2$ is hydrogen.

Suitable product β-hydroxynitriles include, but are not limited to, the following: racemic or chiral 3-hydroxyvaleronitrile (3-hydroxypentanenitrile) and racemic or chiral 3-hydroxybutanenitrile. A preferred β-hydroxynitrile is 3-hydroxyvaleronitrile. Chiral species of 3-hydroxyvaleronitrile are (R)-3-hydroxyvaleronitrile and (S)-3-hydroxyvaleronitrile.

The present process employs inorganic cyanides as reactants with β-hydroxynitriles. Suitable inorganic cyanides include, but are not limited to, the following: potassium cyanide, sodium cyanide, and copper cyanide. Potassium cyanide is preferred.

The present process is carried out in an aqueous organic solvent. Suitable aqueous organic solvents include, but are not limited to, those containing methanol, ethanol, isopropanol, or ethers such as tetrahydrofuran or dimethoxyethane. Water content should be at a level such that the buffer and the epoxide and the cyanide are all at least partially soluble in the reaction mixture. Water content will typically range from between about 10 volume percent (vol %) to about 90 vol %, and more preferably from between about 40 vol % to about 60 vol %, based upon the total volume of the aqueous organic solvent.

EXAMPLES

Racemic 3-Hydroxyvaleronitrile and (R)-(+)-3-Hydroxyvaleronitrile were prepared in accordance with the process of the present invention.

Example 1

Laboratory Synthesis of Racemic 3-Hydroxyvaleronitrile

A 1 liter (L) jacketed glass reaction vessel equipped with a mechanical stirrer, temperature probe, addition funnel and a gas outlet connected to an aqueous sodium hydroxide scrubber was charged with potassium cyanide (41.1 grams (g), 631 millimoles (mmol), 0.9 equivalents (eq.)) and sodium bicarbonate (58.25 g, 693 mmol, 1.0 eq.). A recirculating bath was connected to a reactor jacket and set to 20° C. The reactor was then charged with 150 milliliters (mL) of methanol and 150 mL of deionized water. The reaction mixture was agitated vigorously for a period of about 30 minutes, and 1,2-epoxybutane (50.0 g, 693 mmol, 1.0 eq.) was added to the reaction mixture via an addition funnel over a period of about 15 minutes while the reaction temperature was maintained between 20–24° C. After the addition of 1,2-epoxybutane was complete, the temperature was gradually increased to about 28° C. over a period of about 15 minutes. The reaction mixture was then stirred overnight for a period of about 17 hours. The addition funnel was replaced with a distillation apparatus, and the batch was distilled at atmospheric pressure to remove most of the low boiling components, mainly methanol, from the reaction mixture. After most of the methanol had been distilled (head temperature=72° C.), the pot of the distillation apparatus was charged while still hot with acetonitrile (1100 mL total, in portions of 500 mL, 500 mL, and 100 mL) and the distillation was continued to remove water by means of an acetonitrile-water azeotrope. As the water was depleted from the reaction mixture, solids precipitated on the wall of the distillation vessel. The distillation was continued until the head temperature reached 75° C. The product mixture in the distillation pot was cooled to 20° C. and held overnight. The product mixture contained 5.6 wt % water by Karl-Fisher analysis. The product mixture was drained from the distillation vessel as an oil. The precipitated solids were rinsed with acetonitrile (400 mL), the acetonitrile was removed by rotary evaporator, and the resulting oil was combined with the product mixture. The combined material was concentrated under vacuum to remove volatile materials, primarily acetonitrile, and then the oil was distilled under vacuum to afford the racemic 3-Hydroxyvaleronitrile (53.47 g, 539 mmol, 85% yield) as a colorless oil: boiling point (bp) 90° C.–105° C. (2–3 torr); $^1$H NMR (CDCl$_3$)δ 3.82 (m, 1H), 3.05 (s, 1H), 2.5 (m, 2H), 1.59 (m, 2H), 0.95 (t, J=7 Hz, 3H). NMR is nuclear magnetic resonance spectroscopy.

Example 2

Kilo Laboratory Synthesis of (R)-(+)-3-Hydroxyvaleronitrile

A 12L 4-necked round-bottomed flask equipped with a mechanical stirrer, temperature probe, addition funnel, and a reflux condenser with a gas outlet connected to an aqueous sodium hydroxide scrubber was employed. The flask was charged with potassium cyanide (821 g, 12.61 mol, 0.9 eq.), NaHCO$_3$ (1165 g, 13.87 mol, 1.0 eq.), methanol (3L), and water (3L). There was a mild exotherm upon mixing as the temperature rose from 20° C. to about 25° C. The reaction mixture was stirred for 30 minutes as the temperature was brought to about 22° C. with a water bath. (R)-(+)-1,2-epoxybutane (1000 g, 13.87 mol, 1.0 eq.) was then added to the reaction mixture in 100 mL increments over about 1.75 hours while the temperature was maintained between 18.0–22.6° C. with intermittent use of an ice-bath. The batch was allowed to stir at ambient temperature for about 13 hours overnight. The batch temperature the following morning was 20.9° C. The reaction vessel was equipped with a distillation apparatus, and the reaction mixture was distilled at atmospheric pressure to remove most of the low boiling components, mostly methanol, from the reaction mixture. After most of the methanol had been removed (head temperature=79° C.), the distillation pot was charged while still hot with acetonitrile (18L total, in portions of 2–4L) and the distillation was continued over the course of several days to remove water by means of an acetonitrile-water azeotrope. As the water was depleted from the reaction mixture, solids precipitated on the wall of the distillation vessel. The distillation was continued until the head temperature reached 78° C. The product mixture in the distillation pot was cooled to 20° C. and held overnight. A 2L coarse glass frit was charged with 257 g of silica gel that was pre-conditioned with acetonitrile. The product mixture was filtered through the silica gel. The precipitated solids were rinsed twice with acetonitrile (500 mL), and the combined filtrates were concentrated under vacuum to remove volatile materials, primarily acetonitrile, to afford 1283 g of the (R)-(+)-3-Hydroxyvaleronitrile as a pale yellow oil. The oil was distilled under vacuum to afford the (R)-(+)-3-Hydroxyvaleronitrile of 97 area percent purity by gas chromatography analysis overall purity and 100% enantiomeric excess (1078 g, 539 mmol, 86% yield) as a colorless oil: bp of 100° C.–105° C. (0.45 torr); $^1$H NMR (CDCl$_3$)δ 3.82 (m, 1H), 3.25 (s, 1H), 2.5 (m, 2H), 1.59 (m, 2H), 0.95 (t, J=7 Hz, 3H).

Example 3

Pilot Plant Synthesis of (R)-(+)-3-Hydroxyvaleronitrile

A 50-gallon nitrogen-purged glass-lined reactor with the jacket temperature set to 20° C. was charged with deionized water (45 kg), potassium cyanide (12.3 kg, 188.9 mol), sodium bicarbonate (17.5 kg, 208.3 mol), and methanol (36.1 kg). The batch was agitated for about 30 minutes then charged with (R)-(+)-1,2-epoxybutane (15 kg, 208.0 mol) over a period of about 6 hours while the temperature was maintained between about 19–24° C. The batch was agitated overnight for about 12 hours. The reactor was set for atmospheric distillation, and the batch was distilled at atmospheric pressure until the batch temperature was higher than 85° C. The batch was cooled to 80° C., and acetonitrile (235.8 kg) was added in portions and the distillation was continued. After approximately half of the acetonitrile had been distilled, the batch was cooled, filtered on an Aurora filtration device to remove accumulated precipitated solids, and the filtrate was charged into the reactor. The distillation of acetonitrile was continued until the water content of the batch was <3 wt % by Karl-Fisher analysis, and the batch was cooled. An Aurora filter was charged with dry silica gel (15.4 kg) and the silica gel was wetted with acetonitrile (24.7 kg). The excess acetonitrile was drawn off and sodium sulfate (3 kg) was carefully layered onto the silica gel bed. The silica gel/sodium sulfate filtration medium was covered with a filter cloth, and the batch was filtered through the silica gel/sodium sulfate filtration medium. The batch was charged back into the reactor, the reactor was set for atmospheric distillation, and the batch was distilled to the minimum stirrable volume to afford 22.0 kilograms (kg) of a solution of the (R)-(+)-3-Hydroxyvaleronitrile in acetonitrile. The solution was found to contain 16.23 kg (86% yield) of (R)-(+)-3-Hydroxyvaleronitrile.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for making a water-soluble β-hydroxynitrile represented by the formula:

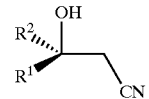

said process comprising the step of:
reacting a 1,2-epoxide and an inorganic cyanide salt in an aqueous organic solvent in the presence of a buffer to form a β-hydroxynitrile; wherein said 1,2-epoxide is represented by the formula:

wherein:
each $R^1$ and $R^2$ is independently selected from the group consisting of: hydrogen, methyl, ethyl, n-propyl, i-propyl, t-butyl, $(CH_2)_nX$, $COR^3$, $CO_2R^3$ and $S(O)_m R^3$;
each X is independently selected from the group consisting of: phenyl, $COR^3$, $CO_2R^3$, $S(O)_m R^3$, $OR^3$, and $N(O)R^3R^4$;
each $R^3$ and $R^4$ is independently selected from the group consisting of: hydrogen, methyl and ethyl;
each n is independently 1 or 2; and
each m is independently 0, 1, 2 or 3.

2. The process of claim 1, wherein said buffer has a p$K_a$ of between about 9.1 to about 13.

3. The process of claim 2, wherein said buffer has a p$K_a$ of between about 10 to about 12.

4. The process of claim 1, wherein said buffer is at least one selected from the group consisting of: sodium bicarbonate, potassium bicarbonate, phenol, succinimide, benzenesulfonamide, and combinations thereof.

5. The process of claim 4, wherein said buffer is sodium bicarbonate.

6. The process of claim 1, wherein said β-hydroxynitrile is selected from the group consisting of: 3-hydroxyvaleronitrile and 3-hydroxybutanenitrile.

7. The process of claim 6, wherein said β-hydroxynitrile is 3-hydroxyvaleronitrile.

8. The process of claim 1, wherein each $R^1$ and $R^2$ is independently selected from the group consisting of: hydrogen, methyl, ethyl and n-propyl.

9. The process of claim 8, wherein said 1,2-epoxide is 1,2-epoxybutane.

10. The process of claim 1, wherein said inorganic cyanide salt is selected from the group consisting of: potassium cyanide, sodium cyanide, and copper cyanide.

11. The process of claim 10, wherein said inorganic cyanide salt is potassium cyanide.

12. The process of claim 1, wherein said inorganic cyanide salt is potassium cyanide, wherein said 1,2-epoxide is 1,2-epoxybutane, wherein said β-hydroxynitrile is 3-hydroxyvaleronitrile, and wherein said buffer is sodium bicarbonate.

13. The process of claim 1, wherein said organic solvent is selected from the group consisting of at least one of: methanol, ethanol, isopropanol, tetrahydrofuran, and dimethoxyethane.

14. The process of claim 1, wherein said aqueous organic solvent comprises aqueous methanol.

15. The process of claim 1, wherein said aqueous organic solvent has a water content of between about 10 vol % to about 90 vol %, based on the total volume of said aqueous organic solvent.

16. The process of claim 15, wherein said aqueous organic solvent has a water content range between about 40 vol % to about 60 vol %, based on the total volume of said aqueous organic solvent.

17. The process of claim 1, further comprising removing at least a portion of the water in said aqueous organic solvent by azeotropic distillation with acetonitrile to produce said β-hydroxynitrile and an azeotropic distillate.

18. The process of claim 17, wherein said azeotropic distillate comprises between about 15 wt % to about 17 wt % water and between about 83 wt % to about 85 wt % acetonitrile when said azeotropic distillation is carried out at atmospheric pressure at a temperature of between about 76° C. to about 82° C.

19. The process of claim 17, further comprising purifying said β-hydroxynitrile by filtration and/or vacuum distillation.

20. The process of claim 1, wherein said 1,2-epoxide is (R)-(+)-1,2-epoxybutane and said β-hydroxynitrile is (R)-(+)-3-hydroxyvaleronitrile.

21. The process of claim 1, wherein each $R^1$ and $R^2$ is independently selected from the group consisting of: hydrogen, methyl, ethyl, n-propyl, i-propyl, t-butyl, $COR^3$, and $CO_2R^3$; each $R^3$ is independently selected from the group consisting of: hydrogen, methyl and ethyl; each n is independently 1 or 2; and each m is independently 0, 1, 2 or 3.

22. A process for making a water-soluble β-hydroxynitrile, comprising the step of:

reacting a 1,2-epoxybutane and an inorganic cyanide salt in an aqueous organic solvent in the presence of a buffer to form 3-hydroxyvaleronitrile.

* * * * *